(12) United States Patent
Shingai et al.

(10) Patent No.: US 6,723,872 B2
(45) Date of Patent: Apr. 20, 2004

(54) PRODUCTION PROCESS FOR HYDROXYALKYL ESTER

(75) Inventors: Yasuhiro Shingai, Himeji (JP); Kouji Deguchi, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/058,377

(22) Filed: Jan. 30, 2002

(65) Prior Publication Data

US 2002/0111510 A1 Aug. 15, 2002

(30) Foreign Application Priority Data

Feb. 9, 2001 (JP) ........................................ 2001-034266

(51) Int. Cl.$^7$ ................................................ C07C 67/26
(52) U.S. Cl. ...................... 560/209; 560/112; 560/200; 560/240
(58) Field of Search ................................ 560/209, 112, 560/200, 240

(56) References Cited

U.S. PATENT DOCUMENTS 4,970,333 A * 11/1990 Rabon, Jr. et al. .......... 560/209

FOREIGN PATENT DOCUMENTS

| EP | 1 033 359 A | 9/2000 |
| EP | 1033359 A2 * | 9/2000 |

* cited by examiner

Primary Examiner—Alan L. Rotman
Assistant Examiner—Héctor M Reyes
(74) Attorney, Agent, or Firm—Roylance, Abrams, Berdo & Goodman, L.L.P.

(57) ABSTRACT

The present invention provides: a process in which, when a hydroxyalkyl ester is produced by carrying out a reaction between a carboxylic acid and an alkylene oxide in the presence of a catalyst, the contamination of the hydroxyalkyl ester with water can be inhibited to the maximum limit without washing the inside of a production apparatus together with the raw carboxylic acid or the hydroxyalkyl ester as an aimed product, or without carrying out azeotropic distillation with water and an azeotropic solvent. The process comprises a washing step and thereafter a drying step in the interval of from the stop of a production of the hydroxyalkyl ester till the restart of this production, wherein the washing step is a step of washing the inside of a production apparatus with water and/or an aqueous basic solution, and wherein the drying step is a step of drying under reduced pressure and/or hot-air-drying the inside of the production apparatus.

14 Claims, No Drawings

PRODUCTION PROCESS FOR HYDROXYALKYL ESTER

BACKGROUND OF THE INVENTION

A. Technical Field

The present invention relates to a production process for a hydroxyalkyl ester, which comprises the step of carrying out a reaction between a carboxylic acid and an alkylene oxide in the presence of a catalyst.

B. Background Art

A hydroxyalkyl ester has a very strong affinity for water, and therefore it has a nature of being freely miscible with water. This nature is utilized, and water or steam is generally used for washing a production apparatus for the hydroxyalkyl ester. On the other hand, when the hydroxyalkyl ester is once contaminated with water, it is very difficult to separate them because of the above nature. Therefore, a product as produced just after the washing of the production apparatus had a high water content.

In addition, when the product is contaminated with water, the polymerization of the raw carboxylic acid or the hydroxyalkyl ester as an aimed product is promoted, and it causes troubles such as clogging the apparatus. Moreover, the contamination with water not only caused the product purity to low, but also might cause the gelation at the (co)polymerization if a hydroxyalkyl ester having a high water content was used as a raw monomer and it was polymerized alone or copolymerized with other copolymerizable monomers.

As to a method for inhibiting the contamination with water in the above way, the following method is, for example, considered: a method which involves washing the inside of the production apparatus together with the raw carboxylic acid or the hydroxyalkyl ester as the aimed product, or a method which involves carrying out azeotropic distillation with water and an azeotropic solvent, in order to remove the water in the production apparatus after the production is stopped and the inside of the production apparatus is washed with the water. However, these methods have the following problems. When the washing of the inside of the production apparatus is carried out together with the raw carboxylic acid or the hydroxyalkyl ester as the aimed product, there is a problem that: the loss of these valuable raw material and product is caused; and a plenty of the valuable raw material and product is required; and the economically great loss is caused; and beside, the substitution of liquid at a portion where the liquid is collected, such as a nozzle cannot be carried out sufficiently. In addition, when the azeotropic distillation with water and the azeotropic solvent is carried out, there is a problem that: a distillation apparatus, such as a dehydration column is separately required; and the residual azeotropic solvent has to be removed.

SUMMARY OF THE INVENTION

Object of the Invention

An object of the present invention is to provide a process in which, when a hydroxyalkyl ester is produced by carrying out a reaction between a carboxylic acid and an alkylene oxide in the presence of a catalyst, the contamination of the hydroxyalkyl ester with water can be inhibited to the minimum limit without washing the inside of a production apparatus together with the raw carboxylic acid or the hydroxyalkyl ester as an aimed product, or without carrying out azeotropic distillation with water and an azeotropic solvent.

Disclosure of the Invention

The present inventors diligently studied to solve the above-mentioned problems. As a result, they found that: the problems are solved by carrying out a washing step and thereafter a drying step in the interval of from the stop of the production of the hydroxyalkyl ester till the restart of this production, wherein the washing step is a step of washing the inside of a production apparatus with water and/or an aqueous basic solution, and wherein the drying step is a step of drying under reduced pressure and/or hot-air-drying the inside of the production apparatus. Then, the present invention was completed.

Accordingly, a production process for a hydroxyalkyl ester, according to the present invention, comprises the step of carrying out a reaction between a carboxylic acid and an alkylene oxide in the presence of a catalyst in order to produce the hydroxyalkyl ester, with the production process being characterized by further comprising a washing step and thereafter a drying step in the interval of from the stop of the production of the hydroxyalkyl ester till the restart of this production, wherein the washing step is a step of washing the inside of a production apparatus with water and/or an aqueous basic solution, and wherein the drying step is a step of drying under reduced pressure and/or hot-air-drying the inside of the production apparatus.

These and other objects and the advantages of the present invention will be more fully apparent from the following detailed disclosure.

DETAILED DESCRIPTION OF THE INVENTION

First of all, the outline of the production process for a hydroxyalkyl ester to which the characteristic production process according to the present invention is favorably applicable is explained.

In the first place, the addition reaction between the carboxylic acid and the alkylene oxide is carried out in the presence of a catalyst. The reaction ratio of this addition reaction is often less than 100%, and the resultant reaction liquid generally includes residues such as unreacted carboxylic acid or alkylene oxide at the end of the reaction. Therefore, the above reaction liquid is fed to a step of removing these unreacted residues of raw materials from the reaction liquid. Then, the purification is carried out by distillation as a subsequent final step with the result that the aimed hydroxyalkyl ester is obtained.

Hereinafter, the process for the addition reaction between the carboxylic acid and the alkylene oxide in the presence of the catalyst is explained.

When the present invention is carried out, as to the amount of the raw materials as charged in the reaction between the carboxylic acid and the alkylene oxide, the amount of the alkylene oxide is favorably not less than 1 mol, more favorably in the range of 1.0 to 5.0 mols, still more favorably 1.0 to 3.0 mols, yet still more favorably 1.0 to 2.0 mols, per 1 mol of the carboxylic acid. In the case where the amount of the alkylene oxide as charged is less than 1.0 mol, there are disadvantages in that the reaction ratio is lowered and by-products are increased. In addition, in the case where the amount of the alkylene oxide as charged is too much, especially more than 5 mols, there are disadvantages in economy.

The carboxylic acid usable in the present invention is not especially limited. Examples thereof include acrylic acid, methacrylic acid, acetic acid, propionic acid, butyric acid, maleic acid, fumaric acid, succinic acid, benzoic acid, terephthalic acid, trimellitic acid, and pyromellitic acid. Acrylic acid and methacrylic acid are particularly favorable (These are referred as (meth)acrylic acid.).

In addition, the alkylene oxide usable in the present invention is not especially limited, but has favorably 2 to 6 carbon atoms, more favorably 2 to 4 carbon atoms. Examples thereof include ethylene oxide, propylene oxide, and butylene oxide. Ethylene oxide or propylene oxide is favorable, and ethylene oxide is particularly favorable.

In the present invention, the reaction between the carboxylic acid and the alkylene oxide in the presence of the catalyst can be carried out according to methods generally used for this kind of reaction.

For example, when the reaction is carried out in a batch manner, it is carried out by introducing the liquid alkylene oxide into the carboxylic acid. When the carboxylic acid is solid, the alkylene oxide is introduced after the carboxylic acid is dissolved in a solvent. Then, the alkylene oxide may be added to the carboxylic acid in a lump, continuously, or intermittently. Then, when it is added continuously or intermittently, as is often the case with this kind of reaction, the reaction is continued still after the addition of the alkylene oxide, in other words, the aging is carried out, and thereby the reaction can be completed. In addition, it is not always necessary to initially add the carboxylic acid at one time, and it can be divided to some portions and then added.

In addition, when the reaction is carried out in a continuous manner, it is carried out by continuously adding the carboxylic acid and the liquid alkylene oxide into a reactor such as a tubular or tank reactor, and by continuously extracting the resultant reaction liquid from the reactor. In this case, the catalyst may continuously be supplied together with the raw materials and then continuously be extracted together with the resultant reaction liquid. In case of the reactor such as a tubular reactor, a solid catalyst may be used in a state of filling the reactor, what is called, in a fixed bed manner. In addition, in case of the tank reactor, a solid catalyst may be used in a state of fluidizing together with the reaction liquid in the reactor, what is called, in a fluidized bed manner. In case of these continuous reactions, the reaction liquid may be circulated partially.

As to the addition of the raw carboxylic acid and the raw alkylene oxide to the reactor, they may be added from separate addition lines respectively. They are beforehand blended in a pipe, a line mixer or a mixing tank before they are added to the reactor, and thereafter they may be added. In addition, when the liquid obtained from the reactor outlet is circulated to the inlet of the reactor, or when the unreacted carboxylic acid or the unreacted alkylene oxide is recovered and recycled, these liquids may be added to the reactor after blending them with the raw carboxylic acid and the raw alkylene oxide. However, when the carboxylic acid and the alkylene oxide are added from separate addition lines, the molar ratio of the carboxylic acid in the reaction liquid is excess in the neighborhood where the carboxylic acid is added. Therefore, the respective raw materials are beforehand blended in such as a pipe before they are added to the reactor, and then they may be added thereto.

The reaction temperature is usually favorably in the range of 40 to 130° C., more favorably 50 to 100° C. In the case where the reaction temperature is lower than 40° C., the reaction proceeds very slowly and it is apart from a practical level. On the other hand, in the case where the reaction temperature is higher than 130° C., there are disadvantages in that: the by-products are increased; and when the carboxylic acid as a raw material has an unsaturated double bond, the polymerization of the carboxylic acid or the hydroxyalkyl ester as a product is caused.

In addition, the reaction may be carried out in a solvent for the purpose of mildly carrying out the reaction. As to the solvent, the following conventional solvents can be used: toluene, xylene, heptane, and octane. The pressure in the reaction system depends upon the kinds of raw materials or the mixing ratio, but the reaction is generally carried out under applied pressure.

In addition, when the reaction is carried out, conventional polymerization inhibitors can be used as stabilizers. Examples thereof include: phenol compounds, such as hydroquinone, methylhydroquinone, tert-butylhydroquinone, 2,6-di-tert-butylhydroquinone, 2,5-di-tert-butylhydroquinone, 2,4-dimethyl-6-tert-butylphenol, hydroquinone monomethyl ether, cresol, and tert-butylcatechol; 1,4-phenylenediamines, such as N-isopropyl-N'-phenyl-1,4-phenylenediamine, N-(1,3-dimethylbutyl)-N'-phenyl-1,4-phenylenediamine, N-(1-methylheptyl)-N'-phenyl-1,4-phenylenediamine, N,N'-diphenyl-1,4-phenylenediamine, and N,N'-di-2-naphthyl-1,4-phenylenediamine; amine compounds such as thiodiphenylamine and phenothiazine; copper dialkyldithiocarbamates, such as copper dibutyldithiocarbamate, copper dipropyldithiocarbamate, copper diethyldithiocarbamate, and copper dimethyldithiocarbamate; copper diaryldithiocarbamates, such as copper diphenyldithiocarbamate; nitroso compounds, such as nitrosophenol, N-nitroso diphenylamine, isoamyl nitrite, N-nitroso-cyclohexylhydroxylamine, N-nitroso-N-phenyl-N-hydroxylamine, and their salts; N-oxyl compounds, such as 2,2,4,4-tetramethylazetidine-1-oxyl, 2,2-dimethyl-4,4-dipropylazetidine-1-oxyl, 2,2,5,5-tetramethylpyrrolidine-1-oxyl, 2,2,5,5-tetramethyl-3-oxopyrrolidine-1-oxyl, 2,2,6,6-tetramethylpiperidine-1-oxyl, 4-hydroxy-2,2,6,6-tetramethylpiperidine-1-oxyl, 6-aza-7,7-dimethyl-spiro(4,5) decane-6-oxyl, 2,2,6,6-tetramethyl-4-acetoxypiperidine-1-oxyl, 2,2,6,6-tetramethyl-4-benzoyloxypiperidine-1-oxyl, and 4,4',4"-tris-(2,2,6,6-tetramethylpiperidine-1-oxyl) phosphate; tetraalkylthiuram disulfides, such as tetrabutylthiuram disulfide, tetrapropylthiuram disulfide, tetraethylthiuram disulfide, and tetramethylthiuram disulfide; and methylene blue. The polymerization inhibitors may be used either alone respectively or in combinations with each other. The amount of the polymerization inhibitor as added is favorably in the range of 0.0001 to 1 weight %, more favorably 0.001 to 0.5 weight %, of the carboxylic acid.

In addition, when the occasion demands, the effect of inhibiting the polymerization is further improved if molecular oxygen is further used together.

In the present invention, the unreacted alkylene oxide and/or the unreacted carboxylic acid may further be recovered and recycled as the raw reaction materials of the hydroxyalkyl ester. In this way, the production costs can further be decreased by recycling the unreacted recovered raw materials as the raw reaction materials.

In the present invention, catalysts as used in the reaction between the carboxylic acid and the alkylene oxide are not especially limited, and conventional catalysts as used in this kind of reaction can be used. Examples thereof include at least one member selected from the group consisting of: chromium compounds such as chromium chloride, chromium acetylacetonate, chromium formate, chromium acetate, chromium acrylate, chromium methacrylate, sodium bichromate, and chromium dibutyldithiocarbamate; iron compounds such as iron powder, ferric chloride, iron formate, iron acetate, iron acrylate, and iron methacrylate; and amines, such as trialkylamine, cyclic amines (e.g. pyridine) and their quaternary ammonium salts, and resins having a basic functional group (e.g. tertiary amino groups, quaternary ammonium salts, and pyridinium groups).

The amount of the catalyst as used for carrying out the present invention is not especially limited, but, when the catalyst is a heterogeneous catalyst and the reaction is carried out in a batch manner, the catalyst is usually used in the range of 5 to 50 weight %, particularly favorably 10 to 30 weight %, of the raw carboxylic acid. In addition, when the reaction is carried out in a continuous manner and a tank reactor is used in a fluidized bed manner, the catalyst is usually used in the range of 30 to 90 vol %, favorably 50 to 80 vol %, of the volume of the reaction liquid. In addition, when a tubular reactor is used in a fixed bed manner, the liquid including the raw reaction materials is passed through at a liquid hourly space velocity (LHSV: $hr^{-1}$) of 0.05 to 15, favorably 0.2 to 8. On the other hand, when the catalyst is a homogeneous catalyst, the catalyst is usually used in the range of 0.05 to 10 weight %, particularly favorably 0.1 to 3 weight %, of the raw carboxylic acid.

In the present invention, the resultant crude hydroxyalkyl ester may further be purified when the occasion demands. The purification method is not especially limited, but examples thereof include purification by distillation, more particularly, by distillation with conventional distillation columns, or rectifying columns, such as packed columns, bubble-cap columns, or perforated-plate columns. However, the distillation is not especially limited to these columns. In addition, other means of purification can be carried out in addition to the purification by distillation.

As is mentioned in the above way, the production process for a hydroxyalkyl ester, according to the present invention, is characterized by comprising a washing step and thereafter a drying step in the interval of from the stop of the production of the hydroxyalkyl ester till the restart of this production, wherein the washing step is a step of washing the inside of a production apparatus with water and/or an aqueous basic solution, and wherein the drying step is a step of drying under reduced pressure and/or hot-air-drying the inside of the production apparatus.

In the washing step, either the water or the aqueous basic solution is used, or both of them are used together as a washing liquid to wash the inside of the production apparatus.

As is mentioned in the above way, deionized water, distilled water, or tap water can fitly be used as the water or the water in the aqueous basic solution as used for the washing liquid. However, the water may be water including a comparatively large amount of impurities (for example, ejector water produced in the production process for the hydroxyalkyl (meth)acrylate or other chemical substance, drain water of vapor, or resultant water produced with reaction) in comparison with the above water.

As is mentioned in the above way, deionized water, distilled water, or tap water is used as the water for the washing liquid, and further steam can also be used. Among them, the water favorably has an electric conductivity of not more than 10 mS/m, more favorably not more than 1 mS/m (but 0 is not included), in view of lowering impurities in the water, such as sodium or calcium ion. The water may be used either alone respectively or in combinations with each other.

When at least an aqueous basic solution is used as the washing liquid, it is favorable because there are effects and advantages such that polymerized materials of the raw material or the product as piled in the system can be dissolved and removed.

The aqueous basic solution as used for the washing liquid is an aqueous solution of a basic substance. The basic substance is not especially limited if the basic substance displays basicity when it is dissolved in water, but examples thereof include: oxides, hydroxides, carbonates, and hydrogen carbonates of alkali metals, such as lithium, sodium, potassium, and rubidium; and oxides and hydroxides of alkali earth metals, such as magnesium, calcium, strontium, and barium. Among these, oxides, hydroxides, carbonates, and hydrogen carbonates of alkali metals are favorable, and hydroxides are particularly favorable, in view of dissolving and removing the polymerized materials of the raw material or the product as piled in the system. Furthermore, sodium and potassium are favorable as the alkali metal. The basic substance may be used either alone respectively or in combinations with each other.

In the aqueous basic solution, the concentration of the basic substance is not especially limited, but is favorably in the range of 0.1 to 40 weight %, more favorably 0.5 to 20 weight %, still more favorably 1 to 10 weight %, relative to the weight of the aqueous basic solution. In the case where the concentration of the basic substance is lower than 0.1 weight %, there are tendencies such that polymerized materials are insufficiently removed when they are piled in the system. In the case where the concentration of the basic substance is higher than 40 weight %, there are tendencies such that it takes much time to wash with a solvent after washing with the aqueous basic solution. Therefore, there are disadvantages.

The aqueous basic solution may be used either alone respectively or in combinations with each other having a different kind and concentration of the basic substance.

To the water or the aqueous basic solution as used for the washing liquid, various additives such as the following surfactants can be added in order to improve the washing effect: alkylene sulfate compounds, benzene sulfonate compounds, sulfosuccinic acid dialkyl ester compounds, amidosulfonate compounds, polyoxyethylene alkylphenol compounds, and polyoxyethylene glycol compounds.

The condition of washing the inside of the production apparatus can freely be selected in consideration for easiness of dissolving solid materials such as polymerized materials or precipitated materials attached to the production apparatus in the washing liquid. However, the washing temperature at the column bottom is, for example, favorably in the range of 50° C. to the boiling temperature of the washing liquid including the solid materials such as the polymerized materials or precipitated materials as washed out, more favorably 80° C. to the boiling temperature. Particularly, alkali steaming such that the aqueous basic solution is used in a state of boiling is favorable. The washing time is also not especially limited. The effect is generally caused within some hours, but the washing can be carried out until the solid materials such as the polymerized materials or precipitated materials are perfectly peeled or dissolved. The pressure is also not especially limited when the washing is carried out, but the washing is favorably carried out under reduced pressure in order to improve the fluidity of the washing liquid in the production apparatus such as a distillation column. When the washing is carried out under reduced pressure, for example, the effect of washing rear trays of the distillation column is improved, and it leads to shortening the washing time. In order to improve the washing effect under reduced pressure, the reduced pressure degree is favorably in the range of 100 to 1,200 hPa, more favorably 150 to 300 hPa.

For example, whether the washing can be carried out with the washing liquid or not can be confirmed by such as the pressure drop of the distillation column, the coefficient of heat transfer of a heat-exchanger, and checking after dismantlement.

When the washing is carried out with the aqueous basic solution, the aqueous basic solution is generally washed and removed with a solvent. This solvent is not especially limited if it can wash and remove the basic substance included in the aqueous basic solution, but water is particularly favorable from the viewpoint of easy availability and handling. Examples thereof include the water as mentioned in the above way, and the favorable one is also mentioned in the above way.

In addition, the condition of washing with the solvent after washing with the aqueous basic solution is also not especially limited. However, for example, the washing is favorably carried out by adjusting the washing temperature at the column bottom to the range of 20° C. to the boiling temperature of the solvent including the aqueous basic solution as washed out in order to improve the washing effect. The washing temperature is more favorably in the range of 50° C. to the boiling temperature, still more favorably 80° C. to the boiling temperature. The pressure at the washing is also not especially limited, but the washing is favorably carried out under reduced pressure in order to improve the fluidity of the washing liquid in the production apparatus such as a distillation column. When the washing is carried out under reduced pressure, for example, the effect of washing rear trays of the distillation column is improved, and it leads to shortening the washing time. In order to improve the washing effect under reduced pressure, the reduced pressure degree is favorably in the range of 100 to 1,200 hPa, more favorably 150 to 300 hPa.

When the washing is carried out with the water after washing with the aqueous basic solution, the pH of the drainage after the washing is adjusted to not more than 9, favorably to the range of 6 to 8 at 50° C. Or when the washing is carried out with the water after washing with the aqueous basic solution, the washing is carried out until the content of the basic substance in the drainage reaches favorably not more than 50 mg/l, more favorably not more than 10 mg/l. When the washing is carried out in this way, the formation of the carboxylic acid by decomposition of the eater can be decreased especially in a purifying step of the hydroxyalkyl ester.

Further more, the washing with a solvent, especially water can beforehand be carried out before washing with the aqueous basic solution. Particularly, when the amount of the polymerized materials to be washed is large, the direct washing with the aqueous basic solution may cause the polymerized materials to swell, and damage to the production apparatus. Therefore, the portion of the polymerized materials soluble in the solvent is beforehand removed, and then the above problem can be prevented.

The condition of washing with the solvent before washing with the aqueous basic solution is also not especially limited. However, for example, the washing is favorably carried out by adjusting the washing temperature at the column bottom to the range of 20° C. to the boiling temperature (at the system pressure then) of the solvent including the polymerized materials (soluble portion in the solvent) as washed out in order to improve the washing effect. The washing temperature is more favorably in the range of 50° C. to the boiling temperature, particularly favorably 80° C. to the boiling temperature. The pressure is also not especially limited when the washing is carried out, but the washing is favorably carried out under reduced pressure in order to improve the fluidity of the washing liquid in the production apparatus such as a distillation column. When the washing is carried out under reduced pressure, for example, the effect of washing rear trays of the distillation column is improved, and it leads to shortening the washing time. In order to improve the washing effect under reduced pressure, the reduced pressure degree is favorably in the range of 100 to 1,200 hPa, more favorably 150 to 300 hPa.

The washing liquid as used for the washing may be recovered and recycled for a new washing step. In this way, the production costs can further be decreased by recycling the recovered washing liquid in the washing step.

In the drying step which is carried out after the washing step, either a drying method under reduced pressure or a hot-air-drying method is used, or both of them are used together as a method for drying the inside of the production apparatus.

When the drying is carried out under reduced pressure, the reduced pressure degree is not especially limited, but it is favorably in the range of 2 to 900 hPa, more favorably 10 to 300 hPa, still more favorably 10 to 100 hPa. In the case where the reduced pressure degree is lower than 2 hPa, it is not economical because a large-scale vacuum apparatus is necessary. In addition, there are tendencies such that it takes much time to reach such a reduced pressure degree. In the case where the reduced pressure degree is higher than 900 hPa, it takes much time to dry. Therefore, there are disadvantages.

When the drying is carried out under reduced pressure, the drying temperature is not especially limited, but it is favorably in the range of 30 to 160° C., more favorably 50 to 140° C., still more favorably 60 to 130° C. In the case where the drying temperature is lower than 30° C., there are tendencies such that it takes much time to dry and the reduced pressure degree has to be settled lower. In the case where the drying temperature is higher than 160° C., there are tendencies such that it is not economical because a large-scale heating apparatus is necessary. Therefore, there are disadvantages.

When the hot-air-drying is carried out, the temperature of the hot air is not especially limited, but it is favorably in the range of 40 to 160° C., more favorably 50 to 150° C., still more favorably 60 to 150° C. In the case where the temperature of the hot air is lower than 40° C., there are tendencies such that it takes much time to dry and it is not economical because a large amount of flowing gas is necessary. In the case where the temperature is higher than 160° C., there are tendencies such that it is not economical because a large-scale apparatus is necessary to generate the hot air. Therefore, there are disadvantages.

When the drying is carried out by only drying under reduced pressure, the drying time is not especially limited, but it is favorably in the range of 0.2 to 24 hours, more favorably 0.2 to 15 hours, more favorably 0.2 to 10 hours. In the case where the drying time is shorter than 0.2 hour, there are tendencies such that the drying of the inside of the production apparatus is insufficiently carried out. In the case where the drying time is longer than 24 hours, there are tendencies such that it is not economical because a large amount of energy is necessary to maintain the reduced pressure degree. Therefore, there are disadvantages.

When the drying is carried out by only hot-air-drying, the drying time is not especially limited, but it is favorably in the range of 0.2 to 24 hours, more favorably 0.2 to 15 hours, more favorably 0.2 to 10 hours. In the case where the drying time is shorter than 0.2 hour, there are tendencies such that the drying of the inside of the production apparatus is insufficiently carried out. In the case where the drying time is longer than 24 hours, there are tendencies such that it is not economical because a large amount of energy is necessary to generate the hot air. Therefore, there are disadvantages.

When the drying under reduced pressure and the hot-air-drying are used together as the drying method, the total drying time is not especially limited when they are used, but it is favorably in the range of 0.5 to 24 hours, more favorably 0.5 to 12 hours, more favorably 0.5 to 8 hours. In the case where the drying time is shorter than 0.5 hour, there are tendencies such that the drying of the inside of the production apparatus is insufficiently carried out. In the case where the drying time is longer than 24 hours, there are tendencies such that it is not economical because a large amount of energy is necessary to maintain the reduced pressure degree or to generate the hot air. Therefore, there are disadvantages.

When the drying under reduced pressure and the hot-air-drying are used together as the drying method, the turn of carrying out them is not especially limited, but it is favorable that the drying under reduced pressure is carried out at first and then the hot-air-drying is carried out in view of shortening the drying time.

Incidentally, when the drying under reduced pressure is carried out, and for example, when nozzle portions to settle instruments and connecting portions for piping is insufficiently heated or thermally insulated, water is frozen and then it cannot be removed. Therefore, it is favorable that: in addition to a heating equipment and a thermally insulating equipment for the whole apparatus, the portions where the heating and the thermally insulating is easily and insufficiently carried out have a heating equipment and a thermally insulating equipment for these portions. In addition, it is also favorable to carry out these operations from a viewpoint of efficiently removing water collected in the corner of the inside of the apparatus. The method for heating or thermally insulating is not especially limited, but examples thereof include a method that involves carrying out thermal insulation such as attaching a temperature-keeping material, or a method that involves settling a warm-water tracing or a steam tracing.

In the present invention, a pressurizing blowing step, which involves blowing the inside of the production apparatus with an incondensable and inert gas under applied pressure between the washing step and the drying step, may be carried out when the occasion demands. When the pressurizing blowing step is carried out, there are advantages in that water can also be removed and the contamination of the hydroxyalkyl ester with water can further be decreased, wherein the water is collected in the corner of the inside of the apparatus, such as nozzle portions to settle instruments and connecting portions for piping.

The incondensable and inert gas as used in this pressurizing blowing step is not especially limited, but examples thereof include nitrogen, helium, argon, air, and carbon dioxide. Among these, nitrogen and air are favorable in view of economy and availability. The incondensable and inert gas may be used either alone respectively or in combinations with each other.

The blowing pressure of the above gas is not especially limited, but it is favorably in the range of 0.01 to 1 MPa, more favorably 0.03 to 0.5 MPa, still more favorably 0.05 to 0.3 MPa. In the case where the blowing pressure of the gas is lower than 0.01 MPa, there are tendencies such that water collected in the corner of the inside of the apparatus cannot be removed efficiently. In the case where the pressure is higher than 1 MPa, there are tendencies such that it is not economical because the production apparatus requires much higher pressure durability. Therefore, there are disadvantages.

The temperature of the above gas is not especially limited, but it is favorably in the range of 0 to 90° C., more favorably 5 to 70° C., still more favorably 5 to 50° C. In the case where the temperature of the gas is lower than 0° C., there are tendencies such that the residual water of the inside of the production apparatus is frozen and cannot be removed outside of the system. In the case where the temperature is higher than 90° C., there are tendencies such that it is not economical because a large amount of energy is necessary to heat the gas. Therefore, there are disadvantages.

When the pressurizing blowing is carried out, it is favorable that its frequency is not once but twice or more in view of shortening the drying time.

The pressurizing blowing method is not especially limited, but the following method is, for example, favorable in view of removing water collected in nozzle portions to settle instruments: a method which involves settling such a valve and a cock for blowing gas at these respective nozzles, and blowing gas by opening these valve and cock.

Incidentally, the above-mentioned washing step and drying step (if necessary, and further the pressurizing blowing step) are carried out in the interval of from the stop of the production of the hydroxyalkyl ester till the restart of the production. However, its frequency of these respective steps is not limited to once but may be twice or more in a period in the interval of from the stop of the production till the restart of the production. For example, a series of operation, which comprises carrying out the washing step and thereafter (if necessary, the pressurizing blowing step is further carried out) carrying out the drying step, is not only carried out once but also may be repeated twice or more.

In addition, the inside of the production apparatus where the above-mentioned washing step and the drying step (if necessary, and further the pressurizing blowing step) are carried out is not especially limited, but examples thereof include the insides of such as a reaction apparatus, a distillation apparatus, a raw material tank, an intermediate tank, a product tank, and a raw-material-recovering apparatus.

(Effects and Advantages of the Invention):

According to the present invention, in a production process for a hydroxyalkyl ester comprising the step of carrying out a reaction between a carboxylic acid and an alkylene oxide in the presence of a catalyst in order to produce the hydroxyalkyl ester, the contamination of the hydroxyalkyl ester with water can be inhibited to the minimum limit without washing the inside of a production apparatus together with the raw carboxylic acid or the hydroxyalkyl ester as an aimed product, or without carrying out azeotropic distillation with water and an azeotropic solvent.

DETAILED DESCRIPTION OF THE PREFERRED EMBODIMENTS

Hereinafter, examples and comparative examples of the present invention are more specifically illustrated. However the present invention is not limited to the following examples.

EXAMPLE 1

A gas, which was in an autoclave of 200 L in capacity equipped with a thermometer, a heating and cooling apparatus, and a stirrer, was replaced with nitrogen gas having an oxygen concentration of 5 vol %. Thereafter, 80 kg of raw acrylic acid was charged therein, and 200 g of phenothiazine and 500 g of hydroquinone monomethyl ether as a polymerization inhibitor, and 3 kg of iron acrylate as a catalyst were added thereto. Next, the liquid temperature in the autoclave was raised to a reaction temperature of 70° C. Then, 60 kg of ethylene oxide was supplied over a period of about 4 hours at a nearly constant feeding speed with a liquid-feeding pump from a pressure-durable receptacle containing the ethylene oxide to the autoclave through a piping attached to the autoclave. In the mean while, the reaction was carried out while the temperature was maintained at 70° C. Then, the reaction was continued for 5 hours while the temperature was maintained at 70° C. Thereafter, the concentration of the acrylic acid was 0.7 weight % when the reaction liquid was analyzed. Therefore, the reaction liquid was cooled immediately. After cooling, the reaction liquid including 2-hydroxyethyl acrylate as formed was extracted from the autoclave and transferred to a distillation column equipped with a shell-and-tube heat exchanger (column diameter: 150 mm), and the distillation was carried out for 5 hours under the following condition: 75 to 85° C. under reduced pressure of 5 hPa.

After the distillation was completed, the washing of the inside of the distillation column was carried out in the following way. In order to remove the residual 2-hydroxyethyl acrylate in the bottom of the distillation column, water was added to the inside of the distillation column in an amount of about ¼ volume of the inside of the distillation column, and the extraction procedure was repeated thrice. Thereafter, in order to wash the top of the distillation column with steam, water was added to the inside of the distillation column, and then this water was boiled with a shell-and-tube heat exchanger as settled outside, and the heating state was kept for one hour (under ordinary pressure). Thereafter, the heating with the shell-and-tube heat exchanger was stopped, and the liquid in the column was extracted. This procedure was further repeated twice.

Next, the pressurizing blowing of the inside of the distillation column was carried out in the following way. The inside of the distillation column was pressurized to 0.1 MPa with air. Thereafter, in order to remove the liquid collected in nozzle portions of a pressure gauge, a thermometer, and a liquid-surface mater as equipped in the distillation column outside of the system, water was scattered by opening valves for blowing gas as settled at these respective nozzles, and by blowing gas (air) under applied pressure for about some minutes (blowing pressure of gas: 0.1 MPa, and temperature of gas: 25° C.).

Next, the drying of the inside of the distillation column was carried out in the following way. The system was returned under ordinary pressure. Thereafter, the system was made under reduced pressure of 50 hPa with a vaporizing ejector, and this reduced pressure degree was maintained for 4 hours to dry the inside of the distillation column under reduced pressure.

After the drying under reduced pressure was completed, air was introduced into the inside of the distillation column to cease the vacuum, and the inside of the distillation column was checked. Thereafter, the distillation of the 2-hydroxyethyl acrylate was restarted in a batch manner. The water content of the first batch distillate (product: 2-hydroxyethyl acrylate) after the distillation was restarted was measured, and then was 1,000 weight ppm. In addition, the formation of polymerized materials was not observed in the distillation column.

EXAMPLE 2

A procedure was carried out in the same way as of Example 1 except for omitting the step of blowing the inside of the distillation column under applied pressure. The water content of the first batch distillate (product: 2-hydroxyethyl acrylate) after the distillation was restarted was measured, and then was 1,500 weight ppm. In addition, the formation of polymerized materials was not observed in the distillation column.

EXAMPLE 3

A procedure was carried out in the same way as of Example 1 except that the heated jacket and shell-and-tube heat exchanger of the main body of the distillation column were heated to 100° C. when the drying of the inside of the distillation column was carried out under reduced pressure. The water content of the first batch distillate (product: 2-hydroxyethyl acrylate) after the distillation was restarted was measured, and then was 700 weight ppm. In addition, the formation of polymerized materials was not observed in the distillation column.

EXAMPLE 4

A procedure was carried out in the same way as of Example 1 except that the washing of the inside of the distillation column was carried out in the following way.

After the distillation was completed, in order to remove the residual 2-hydroxyethyl acrylate in the bottom of the distillation column, water was added to the inside of the distillation column in an amount of about ¼ volume of the inside of the distillation column, and the extraction procedure was repeated twice. Thereafter, in order to wash the top of the distillation column with steam, water was added to the inside of the distillation column in an amount of about ½ volume of the inside of the distillation column, and then this water was boiled with a shell-and-tube heat exchanger as settled outside, and the heating state was kept for one hour (under ordinary pressure). Thereafter, the heating with the shell-and-tube heat exchanger was stopped, and the liquid in the column was extracted. Thereafter, in order to wash polymerized materials in the distillation column, an aqueous sodium hydroxide solution of 4 weight % was added to the inside of the distillation column in an amount of about ½ volume of the inside of the distillation column, and then the aqueous sodium hydroxide solution was heated with the shell-and-tube heat exchanger under ordinary pressure for 2 hours (at 101° C.). Thereafter, the heating with the shell-and-tube heat exchanger was stopped, and the liquid in the column was extracted. Furthermore, the washing procedure with this aqueous sodium hydroxide solution was carried out once more. Thereafter, water was added to the inside of the distillation column in an amount of about ¼ volume of the inside of the distillation column, and the extraction procedure was carried out. Thereafter, in order to wash with steam, water was added to the inside of the distillation column in an amount of about ½ volume of the inside of the distillation column, and then this water was boiled with the shell-and-tube heat exchanger as settled outside, and the heating state was kept for one hour (under ordinary pressure). Thereafter, the heating with the shell-and-tube heat exchanger was stopped, and the liquid in the column was extracted. As to the water used for this water washing, the water having an electric conductivity of 5 mS/m at 25° C. was used. The water washing with the steam was repeated until the pH of the drainage reached 8 at 50° C. The total content of alkali metals and alkali earth metals was 8 mg/l in the drainage when the pH of the drainage reached 8 at 50° C.

The water content of the first batch distillate (product : 2-hydroxyethyl acrylate) after the distillation was restarted was measured, and then was 1,000 weight ppm. In addition, the formation of polymerized materials was not observed in the distillation column.

EXAMPLE 5

A procedure was carried out in the same way as of Example 1 except that the washing of the inside of the distillation column was carried out in the following way.

After the distillation was completed, in order to remove the residual 2-hydroxyethyl acrylate in the bottom of the distillation column, water was added to the inside of the distillation column in an amount of about ¼ volume of the inside of the distillation column, and the extraction procedure was repeated twice. Thereafter, in order to wash the top of the distillation column with steam, water was added to the inside of the distillation column in an amount of about ½ volume of the inside of the distillation column, and then this water was boiled with a shell-and-tube heat exchanger as settled outside, and the heating state was kept for one hour (under ordinary pressure) while this boiling state was kept and while water was supplied from the column top so that the liquid surface would be constant. Thereafter, the heating with the shell-and-tube heat exchanger was stopped, and the liquid in the column was extracted. This procedure was farther carried out once more.

The water content of the first batch distillate (product: 2-hydroxyethyl acrylate) after the distillation was restarted was measured, and then was 1,000 weight ppm. In addition, the formation of polymerized materials was not observed in the distillation column.

EXAMPLE 6

A procedure was carried out in the same way as of Example 1 except that the washing of the inside of the distillation column was carried out in the following way.

After the distillation was completed, in order to remove the residual 2-hydroxyethyl acrylate and polymerized materials in the bottom of the distillation column, an aqueous sodium hydroxide solution of 8 weight % was added to the inside of the distillation column in an amount of about ½ volume of the inside of the distillation column, and then the aqueous sodium hydroxide solution was heated with the shell-and-tube heat exchanger under ordinary pressure to form a boiling state (at 102° C.). The heating state was kept for 3 hours (under ordinary pressure) while this boiling state was kept and while the aqueous sodium hydroxide solution of 8 weight % was supplied to the contact surface of the 2-hydroxyethyl acrylate solution and the steam from the column top so that the liquid surface would be constant. Thereafter, the heating with the shell-and-tube heat exchanger was stopped, and the liquid in the column was extracted. Thereafter, water was added to the inside of the distillation column in an amount of about ¼ volume of the inside of the distillation column, and the extraction procedure was carried out. Thereafter, in order to wash with steam, water was added to the inside of the distillation column in an amount of about ½ volume of the inside of the distillation column, and then this water was boiled with the shell-and-tube heat exchanger as settled outside, and the heating state was kept for one hour (under ordinary pressure). Thereafter, the heating with the shell-and-tube heat exchanger was stopped, and the liquid in the column was extracted. As to the water used for this water washing, the water having an electric conductivity of 5 mS/m at 25° C. was used. The water washing with the steam was repeated until the pH of the drainage reached 8 at 50° C. The total content of alkali metals and alkali earth metals was 20 mg/l in the drainage when the pH of the drainage reached 8 at 50° C.

The water content of the first batch distillate (product: 2-hydroxyethyl acrylate) after the distillation was restarted was measured, and then was 1,000 weight ppm. In addition, the formation of polymerized materials was not observed in the distillation column.

EXAMPLE 7

A procedure was carried out in the same way as of Example 1 except that the hot-air-drying was carried out in the following way instead of the drying under reduced pressure when the drying of the inside of the distillation column was carried out.

After the pressurizing blowing is carried out, the system was returned under ordinary pressure. Thereafter, the inside of the distillation column was hot-air-dried by passing a hot wind (air) at 80° C. into the distillation column with a flow rate of 100 m$^3$/hr for 8 hours.

Thereafter, the distillation of the 2-hydroxyethyl acrylate was restarted in a batch manner. The water content of the first batch distillate (product: 2-hydroxyethyl acrylate) after the distillation was restarted was measured, and then was 2,000 weight ppm. In addition, the formation of polymerized materials was not observed in the distillation column.

EXAMPLE 8

A procedure was carried out in the same way as of Example 3 except that the drying under reduced pressure was carried out, and thereafter the hot-air-drying was further carried out in the following way when the drying of the inside of the distillation column was carried out.

After the drying of the inside of the distillation column is carried out under reduced pressure, the system was returned under ordinary pressure. Thereafter, the inside of the distillation column was hot-air-dried by passing a hot wind (air) at 80° C. into the distillation column with a flow rate of 100 m$^3$/hr for 4 hours.

Thereafter, the distillation of the 2-hydroxyethyl acrylate was restarted in a batch manner. The water content of the first batch distillate (product: 2-hydroxyethyl acrylate) after the distillation was restarted was measured, and then was 500 weight ppm. In addition, the formation of polymerized materials was not observed in the distillation column.

Comparative Example 1

A procedure was carried out in the same way as of Example 1 except that the drying of the inside of the distillation column was not carried out. The water content of the first batch distillate (product: 2-hydroxyethyl acrylate) after the distillation was restarted was measured, and then was 7,000 weight ppm. In addition, the formation of polymerized materials of the 2-hydroxyethyl acrylate was observed in such as nozzle portions of the pressure gauge mater as equipped in the distillation column.

Comparative Example 2

A procedure was carried out in the same way as of Example 1 except that the water washing of the inside of the distillation column was carried out, and thereafter the inside of the distillation column was washed together with the product 2-hydroxyethyl acrylate in the following way without carrying out the pressurizing blowing and drying under reduced pressure.

After the water washing of the inside of the distillation column was carried out, a procedure, which involved adding 2-hydroxyethyl acrylate to the inside of the distillation column in an amount of about ¼ volume of the inside of the distillation column, and extracting it, was repeated thrice.

Thereafter, the distillation of the 2-hydroxyethyl acrylate was restarted in a batch manner. The water content of the first batch distillate (product: 2-hydroxyethyl acrylate) after the distillation was restarted was measured, and then was 3,300 weight ppm. In addition, the formation of polymerized materials of the 2-hydroxyethyl acrylate was observed in such as nozzle portions of the pressure gauge mater as equipped in the distillation column.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A production process for producing a hydroxyalkyl ester, comprising the step of reacting a carboxylic acid and an alkylene oxide in contact with a catalyst in a production apparatus to produce said hydroxyalkyl ester,
   with the production process further comprising a washing step and thereafter a drying step after completion of said production of the hydroxyalkyl ester and before restarting said reaction process of said carboxylic acid and said alkylene oxide,
   wherein said washing step comprises washing an inside of said production apparatus with water, then washing said inside of said production apparatus with an aqueous basic solution and thereafter washing said inside of said production apparatus with water, and wherein said drying step comprises drying said inside of said production apparatus under reduced pressure or hot air.

2. A production process according to claim 1, which further comprises a step of blowing said inside of the production apparatus under pressure with an inert gas that is non-condensable under applied pressure between said washing step and said drying step.

3. A production process according to claim 1, wherein the carboxylic acid is (meth)acrylic acid.

4. A production process according to claim 2, wherein the carboxylic acid is (meth)acrylic acid.

5. A production process according to claim 1, wherein said drying step comprises drying said inside of said production apparatus with hot air while maintaining said production apparatus under reduced pressure.

6. The production process of claim 1, wherein said carboxylic acid is selected from the group consisting of acrylic acid, methacrylic acid, acetic acid, propionic acid, butyric acid, maleic acid, fumaric acid, succinic acid, benzoic acid, terephthalic acid, trimellitic acid and pyromellitic acid.

7. The production process of claim 1, wherein said alkylene oxide contains 2 to 6 carbon atoms.

8. The production process of claim 1, wherein said alkylene oxide is selected from the group consisting of ethylene oxide, propylene oxide and butylene oxide.

9. The production process of claim 1, wherein said catalyst is at least one member selected from the group consisting of chromium compounds, iron compounds and amines.

10. The production process of claim 1, wherein said catalyst is at least one selected from the group consisting of chromium chloride, chromium acetylacetonate, chromium formate, chromium acetate, chromium acrylate, chromium methacrylate, sodium bichromate, chromium dibutyldithiocarbamate, iron powder, ferric chloride, iron formate, iron acetate, iron acrylate, iron methacrylate, trialkylamines and its quaternary ammonium salts, cyclic amines and its quaternary ammonium salts, and resins having a basic functional group.

11. The production process of claim 1, wherein said production apparatus is a tubular or tank reactor.

12. A production process for producing a hydroxyalkyl ester in a production apparatus, said production process comprising
   washing an inside of said production apparatus subsequent to a previous production process of producing said hydroxyalkyl ester, said washing comprising washing said inside of said production apparatus with water, followed by washing with an aqueous basic solution and thereafter washing with water,
   drying said inside of said production apparatus under reduced pressure or by introducing hot air into said production apparatus to remove residual water and reactants from said production apparatus,
   introducing a carboxylic acid, an alkylene oxide and a catalyst into said production apparatus and reacting said carboxylic acid and alkylene oxide in the presence of said catalyst and producing said hydroxyalkyl ester, wherein said alkylene oxide contains 2 to 6 carbon atoms, said carboxylic acid is selected from the group consisting of acrylic acid, methacrylic acid, acetic acid, propionic acid, butyric acid, maleic acid, fumaric acid, succinic acid, benzoic acid, terephthalic acid, trimellitic acid and pyromellitic acid and where said catalyst is at least one member selected from the group consisting of chromium chloride, chromium acetylacetonate, chromium formate, chromium acetate, chromium acrylate, chromium methacrylate, sodium bichromate, chromium dibutyldithiocarbamate, iron powder, ferric chloride, iron formate, iron acetate, iron acrylate, iron methacrylate, trialkylamines and its quaternary ammonium salts, cyclic amines and its quaternary ammonium salts, and resins having a basic functional group.

13. The production process of claim 12, further comprising the step of blowing a non-condensable inert gas into said production apparatus under pressure after said washing and before said drying.

14. The production process of claim 12, wherein said drying comprises introducing hot air into said production apparatus while maintaining said production apparatus under reduced pressure.

* * * * *